United States Patent

Ingomar et al.

Patent Number: 5,254,583
Date of Patent: Oct. 19, 1993

[54] SALTS OF 2-(2,6-DICHLOROANILINO)-PHENYLACETIC ACID, A PROCESS FOR THEIR PREPARATION AND THEIR USE FOR PHARMACEUTICAL PREPARATIONS TO BE APPLIED LOCALLY

[75] Inventors: Grafe Ingomar, Nürnberg; Schickaneder Helmut, Eckental; Mörsdorf J. Peter, Langenzenn; Vergin Hartmut; Ahrens Kurt-Henning, both of Nürnberg, all of Fed. Rep. of Germany

[73] Assignee: Heumann Pharma GmbH & Co., Nuremberg, Fed. Rep. of Germany

[21] Appl. No.: 831,477

[22] Filed: Feb. 5, 1992

[30] Foreign Application Priority Data

Feb. 7, 1991 [EP] European Pat. Off. ........ 91101674.9

[51] Int. Cl.$^5$ .................... A01N 55/02; A01N 37/12; C07C 229/00
[52] U.S. Cl. ................................. 514/492; 514/567; 562/456
[58] Field of Search .................. 562/456; 560/42; 514/647, 492, 567

[56] References Cited

U.S. PATENT DOCUMENTS 3,558,690  1/1971  Sallmann et al. .................. 260/471

FOREIGN PATENT DOCUMENTS 0245126   4/1987  European Pat. Off. .
3720896   1/1988  Fed. Rep. of Germany .
3336047  12/1989  Fed. Rep. of Germany ...... 562/456

*Primary Examiner*—José G. Dees
*Assistant Examiner*—Keith MacMillan
*Attorney, Agent, or Firm*—Burns, Doane, Swecker & Mathis

[57] ABSTRACT

New salts of 2-(2,6-dichloroanilino)-phenylacetic acid corresponding to the general formula (I)

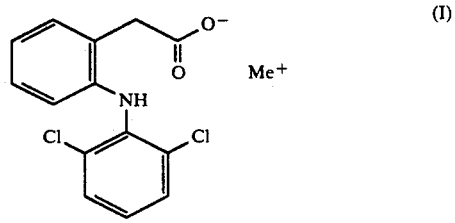

in which Me stands for a rubidium or caesium atom, a process for the preparation of these salts and pharmaceutical preparations containing these salts are described. The new salts and pharmaceutical preparations containing the salts can be used successfully for the treatment of inflammatory and rheumatic processes and painful conditions.

5 Claims, No Drawings

SALTS OF 2-(2,6-DICHLOROANILINO)-PHENYLACETIC ACID, A PROCESS FOR THEIR PREPARATION AND THEIR USE FOR PHARMACEUTICAL PREPARATIONS TO BE APPLIED LOCALLY

This invention relates to new salts of 2-(2,6-dichloroanilino)-phenylacetic acid, to a process for their preparation and to pharmaceutical preparations containing these salts.

Diclofenac is the INN name of the compound 2-(2,6-dichloroanilino)-phenylacetic acid which belongs to the group of non-steroidal anti-inflammatory agents and corresponds to the following formula:

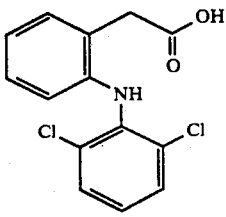

For the therapy of inflammatory and rheumatic processes and the alleviation of pain, the compound is used in the form of its sodium salt which is readily soluble in water and alcohols. It has excellent antiphlogistic and analgesic actions. Preferred galenic formulations are tablets, coated tablets, capsules, injectable solutions and suppositories. Since various side effects such as gastro-intestinal complaints and disturbances in the kidney and liver functions may occur, in particular in response to oral administration, it would be desirable to obtain topical preparations of salts of 2-(2,6-dichloroan-ilino)-phenylacetic acid, i.e. preparations which can be applied percutaneously, as these can directly reach the target organ, e.g. the diseased joint. Further, such a preparation would eliminate the possibility of initial metabolisation in the liver, which is unavoidable in the case of oral administration.

Although locally applied pharmaceutical compositions based on an oil/water emulsion containing the diethylammonium salt of 2-(2,6-dichloroanilino)-phenylacetic acid have already been described in DE-OS 33 36 047 (GB 2,128,087), diethylamine entails the risk of formation of carcinogenic nitrosamines. The Federal Health Department therefore published a recommendation in the Spring of 1987 that secondary amines which tend to form nitrosamines should not be used in pharmaceutical preparations and cosmetic products.

DE-OS 37 20 896 (GB 2 192 539) describes pharmaceutical compositions, in particular for transdermal therapeutic systems, containing 2-(2,6-dichloroanilino)-phenylacetic acid or a pharmaceutically usable salt thereof, in particular the sodium, potassium or diethylammonium salt, together with a compound which increases the capacity for permeation.

It is therefore an object of the present invention to provide new salts of 2-(2,6-dichloroanilino)-phenylacetic acid which have improved properties and pharmaceutical preparations with improved penetration properties suitable for local application.

This problem is solved according to the invention by means of new salts of 2-(2,6-dichloroanilino)-phenylacetic acid corresponding to the general formula (I)

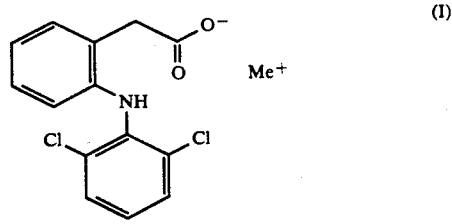

wherein Me stands for a rubidium or caesium atom.

The alkali metal salts of 2-(2,6-dichloroanilino)-phenylacetic acid according to the invention have not hitherto been described in the literature. They are high melting, stable solids which are distinguished by an unexpectedly high lipophilic character, i.e. they have a relatively low salt character. Thus both are only very moderately soluble in water but readily soluble in apolar, organic solvents, e.g. in ketones such as methyl isobutyl ketone. The rubidium salt and the caesium salt are distinguished from all salts of 2-(2,6-dichloroanilino)-phenylacetic acids hitherto described by an unexpectedly high absorption through the skin.

The salts according to the invention are prepared by a process which is characterised in that 2-(2,6-dichloroanilino)-phenylacetic acid or the sodium salt thereof is reacted with a suitable rubidium or caesium salt in aqueous alcoholic solution or in an aqueous organic diphasic system.

Suitable rubidium or caesium salts are the chlorides, bromides, sulphates or carbonates thereof, the carbonates being preferred.

Reaction of the rubidium or caesium salts with 2-(2,6-dichloroanilino)-phenylacetic acid or the sodium salt therof may be carried out in a homogeneous medium of water and a water-miscible lower alcohol, for example methanol, ethanol or isopropanol, or it may be carried out in a diphasic system of an aqueous phase and an organic phase. Suitable organic solvents for this purpose include ethers such as tert.-butyl methyl ether or diethyl ether, esters such as ethyl acetate or ketones such as methyl ethyl ketone or methyl isobutyl ketone, ketones being preferred. The reactants are preferably reacted together in a molar ratio of 1:1 at temperatures from 0° to 80 °C., preferably at room temperature.

Isolation and purification of the new salts of 2-(2,6-dichloroanilino)-phenylacetic acid is carried out by the usual methods, e.g. extraction, precipitation and/or crystallisation from suitable solvents.

Lastly, the invention provides a pharmaceutical preparation which is characterised in that it contains, as active ingredient, a salt of 2-(2,6-dichloroanilino)-phenylacetic acid as defined above, together with a physiologically acceptable organic solvent suitable for topical application and optionally other physiologically acceptable auxiliary substances.

As already indicated above, the salts according to the invention are distinguished from the known salts of 2-(2,6-dichloroanilino)-phenylacetic acid by a surprising and unexpectedly high capacity for absorption through the skin. These surprising properties were demonstrated in the model described below of in vitro skin permeation on hairless rats. Pieces of skin 3.14 cm$^2$ in surface area taken from the thoracico-abdominal region of hairless rats were mounted in a penetration chamber of T. J. Franz (J. Invest. Dermatol. 64, 190 (1975)).

The salts of 2-(2,6-dichloroanilino)phenylacetic acid to be tested were dissolved in ethanol/isopropanol 1:1 (v/v). The weight of the salts was based on 10.0 mg/ml of the sodium salt of 2-(2,6-dichloranilino)-phenylacetic acid. 1 ml of the solutions was applied to the surface of skin sample in each case.

The acceptor liquid consisted of about 8 ml of 1/15M Sorensen phosphate buffer, pH 7.4. The total quantities of 2-(2,6-dichloroanilino)-phenylacetic acid in the whole acceptor liquid where determined by HPLC after 8 hours' permeation in each case.

RESULTS

| Salt of 2-(2,6-di-chloroanilino)-phenylacetic acid | Number of individual experiments | Total quanity of 2-(2,6-dichloroanilino)-phenylacetic acid ($\mu$g) |
| --- | --- | --- |
| Sodium | 10 | 11.2 ± 7.4 |
| Potassium | 19 | 19.0 ± 7.7 |
| Diethylammonium | 5 | 5.2 ± 1.4 |
| Rubidium | 5 | 52.1 ± 9.8 |
| Caesium | 5 | 44.1 ± 10.9 |
| COMPARISON: | | |
| free acid | 6 | 1.6 ± 0.3 |

The pharmaceutical agents for local, percutaneous application may be applied in the form of creams, ointments, gels or pastes.

The usual solvents and auxiliary substances are used for the preparation of these forms of pharmaceutical products. The substances used as the oily phases for creams may be, for example, fatty alcohols, fatty acids, partial fatty acid esters of glycerol or natural or semi-synthetic fats. Suitable paraffins which are liquid at the body temperature or Vaseline oil may be used as the oily phases for ointments. The aqueous phases of creams and ointments may also contain polyhydric alcohols such as glycerol or propylene glycol.

Dimethylsulphoxide, lower alcohols such as ethanol or isopropanol and glycols may be used as solvents in gels.

According to a preferred embodiment of the invention, the pharmaceutical preparations according to the invention contain a compound which increases the permeation.

Examples of such compounds include the amides of higher fatty acids, such as N,N-dimethyl-lauroylamide. Inorganic and organic macromolecules are suitable for use as gel forming materials. Examples of inorganic gel forming compounds include silicates, in particular aluminium and magnesium aluminium silicates, and colloidal silicas. The organic macromolecules used as gel formers may be natural, semi-synthetic or synthetic polymers. Examples of the first two groups include polysaccharides and their derivatives such as starch, gelatine, agar-agar, alginates or carboxymethyl cellulose. Polymers based on vinyl alcohols, vinyl pyrrolidone or acrylic or methacrylic acid derivatives are suitable gel-forming synthetic macro-molecules.

Other auxiliary substances used for the above-mentioned forms of pharmaceutical preparations include emulsifiers such as non-ionic or anionic surfactants, preservatives, perfumes, etc.

The auxiliary agents and carrier materials mentioned above are the usual substances used for the preparation of such forms of pharmaceutical products. Preparation of the pharmaceutical products is also carried out by the known galenic methods; for example, the above-mentioned components and auxiliary substances may be mixed together in the quantities indicated and the mixture obtained may be worked up in known manner to produce the topical formulations.

The pharmaceutical preparations suitable for topical application obtained by these means may be used for the treatment of inflammations and painful conditions, in particular rheumatic diseases, in human and veterinary medicine. Examples of such diseases include inflammatory rheumatic conditions of the joints and spinal column including attacks of gout, irritable conditions in degenerative diseases of the joints and spinal column, rheumatism of the soft tissues and painful swellings or inflammations after injuries or operations. Good results may be expected particularly in the treatment of inflammatory forms of rheumatism or degenerative forms of rheumatism activated by inflammation.

The following Examples serve to illustrate the invention:

EXAMPLE 1

Rubidium salt of 2-(2,6-dichloroanilino)-phenyl acetic acid 44.3 g (150 mmol) of 2-(2,6-Dichloroanilino)-phenylacetic acid are added portionwise to a solution of 17.3 g (75 mmol) of rubidium carbonate in 180 ml of ethanol and 30 ml of water.

After the solution has been briefly stirred, it is concentrated by evaporation under vacuum, dehydrated by azeotropic distillation with 50 ml of methyl isobutyl ketone and again evaporated to dryness under vacuum.

52.0 g (91% of the theory) of coarse, colourless prisms which lose their water of crystallisation at 90° C. and melt at 270° C. are obtained after recrystallisation of the residue from isopropanol.

$C_{14}H_{10}Cl_2NO_2Rb$ (380.62).

EXAMPLE 2

Caesium salt of 2-(2,6-dichloroanilino)-phenylacetic acid 19.61 g (60 mmol) of caesium carbonate and 35.4 g (120 mmol) of 2-(2,6-dichloroanilino)-phenylacetic acid are reacted together analogously to Example 1.

51.0 g (99% of the theory) of colourless scales melting at 245° C. are obtained after recrystallisation from methyl isobutyl ketone.

$C_{14}H_{10}ClCsNO_2$ (428.05).

We claim:

1. A pharmaceutical composition suitable for topical administration comprising an effective anti-inflammatory, anti-rheumatic or analgesic amount of a salt of 2-(2,6-dichloroanilino)-phenylacetic acid having the formula

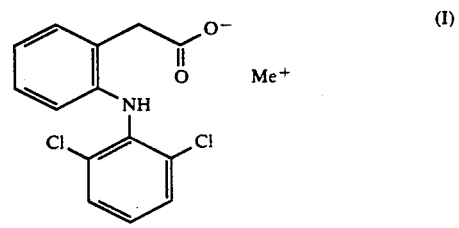

(I)

wherein Me is rubidium or caesium and a physiologically and topically acceptable organic solvent therefor.

2. The pharmaceutical composition according to claim 1, further comprising other physiologically, topically acceptable auxiliary substances.

3. The pharmaceutical composition according to claim 1, wherein the organic solvent is in admixture with water.

4. The pharmaceutical composition according to claim 1, further comprising a permeation enhancer.

5. A pharmaceutical composition according to claim 3, further comprising a permeation enhancer.

* * * * *